(12) United States Patent
Chattopadhyay et al.

(10) Patent No.: US 7,750,165 B2
(45) Date of Patent: Jul. 6, 2010

(54) METAXALONE POLYMORPHS

(75) Inventors: Jayanta Chattopadhyay, Nadia (IN); Subrata Sarkar, Nadia (IN); Jyan Shankar Mahanty, Nadia (IN); Susanta Hazra, Nadia (IN); Moloy Mitra, Ghaziabad (IN); Manoj Kumar Singh, Ghaziabad (IN)

(73) Assignee: Fresenius Kabi Oncology Limited, New Delhi (IN)

( * ) Notice: Subject to any disclaimer, the term of this patent is extended or adjusted under 35 U.S.C. 154(b) by 0 days.

(21) Appl. No.: 11/647,974

(22) Filed: Dec. 29, 2006

(65) Prior Publication Data

US 2007/0185177 A1 Aug. 9, 2007

(30) Foreign Application Priority Data

Dec. 29, 2005 (IN) .................. 1196/KOL/2005

(51) Int. Cl.
*C07D 263/00* (2006.01)
(52) U.S. Cl. ..................................... 548/229
(58) Field of Classification Search ........................ None
See application file for complete search history.

(56) References Cited

U.S. PATENT DOCUMENTS

| 3,062,827 A | 11/1962 | Lunsford |
| 3,446,814 A | 5/1969 | Budnowski |
| 6,407,128 B1 | 6/2002 | Scaife et al. |
| 6,562,980 B1 | 5/2003 | Lee et al. |

FOREIGN PATENT DOCUMENTS

| WO | 03/061552 A2 | 7/2003 |
| WO | 2004/019937 A1 | 3/2004 |
| WO | 2006/082597 A2 | 8/2006 |

OTHER PUBLICATIONS

Brittain, Polymorphism in Pharmaceutical Solids, vol. 95, p. 228-229.*
Chawla et al., "Challenges in Polymorphism of Pharmaceuticals", CRIPS vol. 5, No. 1, Jan.-Mar. 2004 (4 PAGES).*
Newman et al., "Solid-state analysis of the active pharmaceutical ingredient in drug products", DDT vol. 8, No. 19, Oct. 2003, p. 898-905.*
Brittain et al. #2 "Effects of pharmaceutical processing on drug polymorphs and solvates" in Polymorphism in Pharmaceutical Solids, vol. 95, p. 331-361.*
Express-Pharma-Online (http://www.expresspharmaonline.com/20031023/edit02.shtml).*

* cited by examiner

*Primary Examiner*—Golam M. M. Shameem
*Assistant Examiner*—Sun Jae Y Loewe
(74) *Attorney, Agent, or Firm*—Merchant & Gould P.C.

(57) ABSTRACT

The invention provides two crystalline forms A and B of the skeletal muscle relaxant and anxiolytic agent, Metaxalone of formula (I), and a process for preparation thereof. The two crystalline forms A and B are bioavailable. The invention further provides pharmaceutical compositions comprising the two bioavailable crystalline forms, useful for the relief of discomforts associated with acute, painful musculoskeletal conditions.

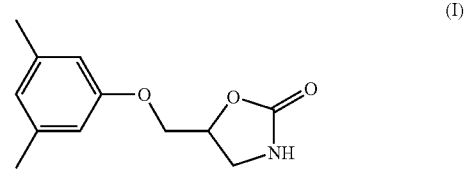

(I)

7 Claims, 8 Drawing Sheets

IR - SPECTRUM OF CRYSTALLINE FORM A OF METAXALONE

IR - SPECTRUM OF CRYSTALLINE FORM B OF METAXALONE

DSC - THERMOGRAM OF CRYSTALLINE FORM A OF METAXALONE

DSC - THERMOGRAM OF CRYSTALLINE FORM B OF METAXALONE

X-RAY (POWDER) DIFFRACTION PATTERN OF CRYSTALLINE FORM B OF METAXALONE

MEAN PLOT OF CONCENTRATION VERSUS TIME OF CRYSTALLINE FORM A AND FORM B OF METAXALONE IN FEMALE WISTAR RAT AT ORAL DOSE OF 150 MG/KG

SEMI LOGARITHMIC MEAN PLOT OF CONCENTRATION VERSUS TIME OF CRYSTALLINE FORM A AND FORM B OF METAXALONE IN FEMALE WISTAR RAT AT ORAL DOSE OF 150 MG/KG

METAXALONE POLYMORPHS

FIELD OF THE INVENTION

The present invention relates to two crystalline forms A and B of Metaxalone of formula (I), which are bioavailable. The present invention further relates to a selective method for the preparation of the two bioavailable crystalline forms A and B of Metaxalone. The present invention also relates to pharmaceutical compositions comprising the bioavailable crystalline forms A and B of Metaxalone, useful for the treatment of discomforts associated with acute, painful musculoskeletal conditions.

BACKGROUND OF THE INVENTION

The chemical entity 5-(3',5'-dimethyl phenoxy)methyl-2-oxazolidinone of formula (I),

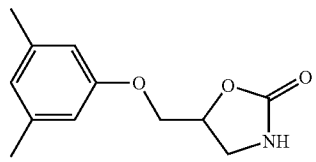

(I)

generically known as Metaxalone, is an interneuronal blocking agent. It is used in physical therapy and other measures to relax muscles and relieve pain and discomfort caused by strains, sprains and other muscle injuries.

The drug, which was approved in January, 1962 in the U.K and in August, 1962 in the USA, has since been marketed under the brand name Skelaxin® for the abovementioned indications.

Inspite of metaxalone being in therapeutic use for the last 43 years, however, it is surprising that it is still not listed by US and European Pharmacopoeias.

Essentially, two methods for the synthesis of Metaxalone have been reported, which are summarized in Schemes-1 and 2 given herein below:

Scheme-1: Method for preparation of Metaxalone

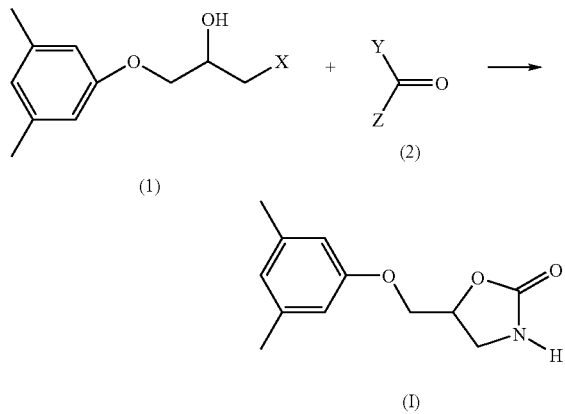

X=OH, NH2, Cl, Carbamate etc.
Y=NH$_2$, O—CH$_3$, O—CCl$_3$, Cl
Z=NH$_2$, O—CH$_3$, O—CCl$_3$, OEt The method summarized in Scheme-1 and as disclosed in U.S. Pat. No. 3,062,827 and WO03061552 comprises the fusion of 3-(phenoxy)-2-hydroxy-propyl-1-substituted compounds (1) with 1, 1 disubstituted carbonyl compounds (2).

Scheme-2: Method for preparation of Metaxalone

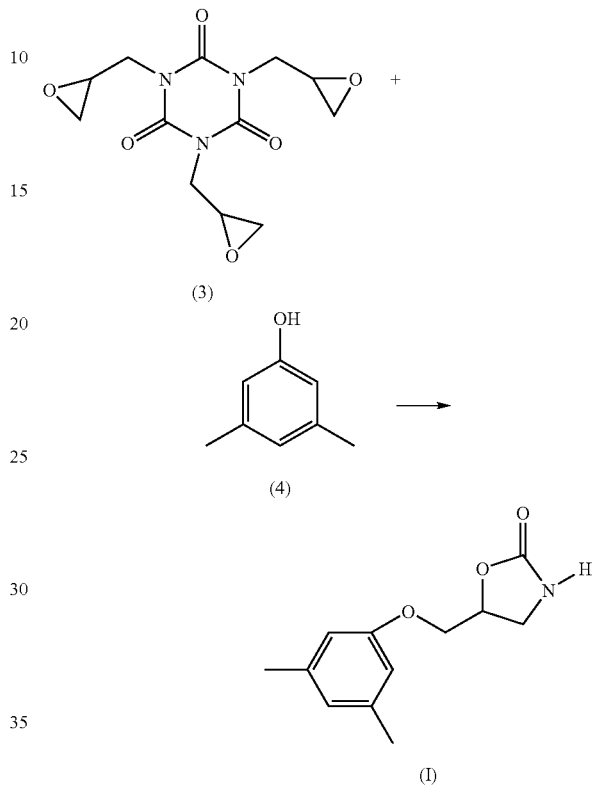

Similarly the method described in Scheme-2 and disclosed in U.S. Pat. Nos. 3,446,814 and 6,562,980 comprises a reaction between Triglycidyl isocyanurate (TGIC, 3) and a suitable Phenol (4).

With regard to the method summarized in Scheme-1, typically the reaction of 3-(phenoxy)-2-hydroxy-propyl-1-substituted compounds (1) with 1, 1 disubstituted carbonyl compound (2) is carried in the presence or absence of solvents at temperatures between 50-150° C. (U.S. Pat. No. 3,062,827) and 170-200° C. (WO03061552) for 3-5 hours. The product i.e. Metaxalone is isolated from solvents like ethyl acetate, benzene, toluene, xylene, cyclohexane, methanol, ethanol, butyl acetate, acetone, methylisobutylketone, ether, tetrahydrofuran, dioxan, dimethoxyethane etc.

Similarly, the method described in Scheme-2 involves a reaction between Triglycidyl isocyanurate (TGIC, 3) and a suitable Phenol (4) in the presence of base and solvents such as benzene, toluene, chlorobenzene, dimethylformamide, dimethyl sulfoxide, acetone etc at reflux temperatures for 12 to 24 hours. The product obtained i.e. Metaxalone is recrystallised from solvents like chlorobenzene, water or ethyl acetate.

While any physical, chemical, or physicochemical properties of Metaxalone isolated from most of the methods mentioned hereinbefore is not disclosed, however, the only report or disclosure of any such properties find mention in the following cases:

i) Crystallization from dry ethyl acetate as disclosed in U.S. Pat. No. 3,062,827, which further mentions the melting point of the product to be 121.5-123° C.;

ii) Crystallization from chlorobenzene as disclosed in U.S. Pat. No. 3,446,814, where the product obtained has a melting point of 122° C.; and iii) Crystallization from benzene, toluene, xylene, cyclohexane, methanol, ethanol, ethyl acetate, butyl acetate, acetone, methylisobutylketone, ether, tetrahydrofuran, dioxan, dimethoxyethane etc., as disclosed in WO03061552, which mentions that the product obtained has purity greater than 99%.

The abovementioned documents, apart from mere mention that the product i.e. Metaxalone could be recrystallised from various solvents mentioned therein do not provide any details of the crystallization conditions or parameters such as temperature, solvent proportion, rate of crystallization etc. This would be particularly evident from the disclosures contained in Example-1 of U.S. Pat. No. 3,062,827 and Example-7 of U.S. Pat. No. 3,446,814.

While Metaxalone has been in clinical practice since 1962 and, moreover, since it is known to be produced by the methods summarized in Schemes-1 and 2, however, because of its low aqueous solubility, the drug product (finished dosage form) or the drug substance [Bulk Active Pharmaceutical Ingredient (API)] made from different manufacturing batches or from different manufacturing locations have not been found to be uniform or consistent in their bioavailability.

Many studies and attempts have been made to address the issue of inconsistent bioavailability, of which two noteworthy disclosures are given hereinbelow:

a) Michael Scaife et al in U.S. Pat. No. 6,407,128 have reported a method to increase the bioavailability of Metaxalone by the administration of an oral dosage form with food, wherein the administration occurs between 30 minutes prior to or 2 hours after consuming food.

b) Dharamadhikari et al in WO2004019937 report that if the Metaxalone used is in a "pharmaceutically acceptable solubility-improved form", the bioavailability is enhanced. "Pharmaceutically acceptable solubility improved form" referred to therein comprises of micronised, high-energy crystalline or amorphous form of Metaxalone or salt form of drug.

Dharamadhikari et al further mention that the "Pharmaceutically acceptable solubility improved form" could be obtained by conventional methods such as milling, crystallization, sublimation, or spray drying etc. or through known methods of forming a solid dispersion of the drug in a carrier such as spray drying, melt dispersion, solvent evaporation etc.

Further, they also recommend addition of excipients like solubilizing agents, surfactants, pH control agents, and complexing agents to enhance the bioavailability.

In addition, Dharamadhikari et al mention the importance of particle size and specific surface area in obtaining the desired bioavailability.

From the teachings of WO2004019937, it would be abundantly evident that the method (s) disclosed therein primarily relate to obtaining a material of reduced particle size or increased surface area which is a technique widely practiced in pharmaceutical area and lacks any innovativeness.

While WO2004019937 mentions utilization of other forms of Metaxalone, such as high energy crystalline/amorphous or salt form, however, like the prior art documents, mentioned hereineearlier, it i.e. WO2004019937 fails to provide any enabling disclosure as to how such forms could be obtained as well as is silent about the bioavailability of the specified forms of Metaxalone.

As mentioned hereinbefore, since the only enabling disclosure contained in WO2004019937 refers to a micronised form it would endorse the present inventors view that WO2004019937 primarily relates to the studies on the bioavailability of a micronised form of Metaxalone.

Micronisation or otherwise referred to as milling requires special machines or equipment which calls for not only capital investment but also increases the cost of manufacture.

To summarize, the prior art methods for the manufacture of Metaxalone:

i) Do not provide any physical, chemical, or physicochemical properties of the product obtained apart from a mere mention of melting point and purity in few cases.

ii) Do not provide any details of the crystallization conditions or parameters such as temperature, solvent proportion, rate of crystallization etc; and iii) Are known to produce products, which in general are found to be inconsistent in their bioavailability.

Further, the only reports related to improvement of bioavailability of Metaxalone prescribe that the drug be either taken along with food or recommend that the bulk drug should be in a form which has a specific particle size or surface area.

The latter especially calls for micronisation techniques, which are not only tedious and lengthy but also result in loss of precious material, thereby increasing the cost of manufacture of Metaxalone.

As the drug i.e. Metaxalone is not listed in the US, EP or for that matter in the Pharmacopoeias of other countries, and, moreover, since there is no Pharmacopoeial Reference Standard available, it would be difficult for a Manufacturer to not only set a specification for his/her product but also to predict whether his/her product would be bioavailable.

Therefore There exists a longfelt need for either a manufacturing process for either the bulk or dosage form of Metaxalone, which would be simple, convenient and economical to produce and which, moreover, would impart consistent bioavailability of the drug substance or drug product.

The present invention is a step forward in this direction and provides crystalline forms of Metaxalone, hitherto unknown and which are bioavailable.

OBJECTS OF THE INVENTION

An object of the present invention is to provide crystalline forms of Metaxalone, which have consistent bioavailablity.

Another object of the present invention is to provide a method for preparation of crystalline forms of Metaxalone, which have consistent bioavailablity.

Yet another object of the present invention is to provide a bioavailable form of Metaxalone, which bioavailability is not dependent on the intake of food.

A further object of the present invention is to provide a bioavailable form of Metaxalone, by a process which does not take recourse to any micronisation or milling technique.

A further object of the present invention is to provide a method for preparation of a bioavailable form of Metaxalone, which is simple, convenient and cost effective.

Another object of the present invention is to provide a pharmaceutical composition comprising the polymorphs of Metaxalone to relax muscles and relieve pain.

Yet another object of the present invention is to provide a method for treatment of pain and discomfort caused by strains, sprains and other muscle injuries comprising administration to humans and animals, a pharmaceutical composition comprising the bioavailable crystalline forms of Metaxalone.

SUMMARY OF THE INVENTION

In their endeavor to meet the objects, the present inventors have found to their surprise that the longfelt need for obtaining Metaxalone which exhibits consistent bioavailability, could be achieved through a rather simple technique of crystallization of Metaxalone which affords certain crystalline forms, hitherto unknown and which, moreover, when utilized for manufacture of a suitable dosage form of the drug provides the requisite bioavailability.

Specifically, the present inventors have found that at least two crystalline forms of Metaxalone could be prepared through control of the rate of crystallization from respective solvents or mixtures thereof.

More specifically, the present inventors have found that crystallization of Metaxalone from an organic solvent or a mixture thereof at a "faster rate" leads to production of a crystalline form of Metaxalone, hereinafter designated as Form A, whereas, a "slower rate of crystallization" leads to the production of another crystalline form of Metaxalone, hereinafter designated as Form B, with the two forms distinct from each other in their physical as well as solid state properties.

SUMMARY OF INVENTION

Thus according a principal aspect of the invention there is provided crystalline Metaxalone Form A comprising an X-ray (powder) diffraction pattern having characteristic peaks at diffraction angles 2-θ of about 4.41, 13.34, and 17.86.

According to another principal aspect of the invention there is provided crystalline Form B of Metaxalone, exhibiting an X-ray (powder) diffraction pattern having characteristic peaks at diffraction angles 2-θ of about 10.26, 14.18, 19.0 and 22.4.

According to another aspect of the invention there is provided a process for preparation of bioavailable crystalline Form A of Metaxalone comprising the steps of (a) dissolving Metaxalone in an organic solvent or mixtures thereof, at a reflux temperature of the said organic solvent or mixtures thereof; (b) cooling the solution of step (a) to a temperature of between 20-35° C. over a period of between 1 to 1.5 hours; (c) cooling the solution of step (b) to a temperature of between 0-5° C.; and (d) collecting the crystals of Metaxalone Form A by filtration.

According to further aspect of the invention there is provided a process for preparation of bioavailable crystalline Form B of Metaxalone comprising the steps of (a) dissolving Metaxalone in an organic solvent or mixtures thereof, at a reflux temperature of the said organic solvent or mixtures thereof; (b) cooling the solution of step (a) to a temperature of between 20-35° C. over a period exceeding 1.5 hours; (c) cooling the solution of step (b) to a temperature of between 0-5° C.; and (d) collecting the crystals of Metaxalone Form B by filtration.

According to a still further aspect of the invention there is provided a pharmaceutical composition comprising crystalline Form A of Metaxalone and pharmaceutically acceptable excipients.

According to yet another aspect of the invention there is provided a pharmaceutical composition comprising crystalline Form B of Metaxalone and pharmaceutically acceptable excipients.

According to another aspect of the invention there is provided a method for the treatment of discomforts associated with acute, painful musculoskeletal conditions comprising administration of a pharmaceutical composition comprising crystalline Form A or Form B of Metaxalone to a patient in need thereof.

Description of Form A and Form B of Metaxalone

Form A of Metaxalone

The crystalline Form A of Metaxalone has a X-ray (powder) diffraction pattern is substantially as depicted in FIG. 5. The said form exhibits an I.R spectrum with $v_{max}$ at about 1728 $cm^{-1}$ and 1738 $cm^{-1}$ for the carbonyl group. The I.R spectrum is substantially as depicted in FIG. 1. The crystalline Form A of Metaxalone exhibits an endotherm at about 122.33° C., in its Differential Scanning Calorimeter (DSC) thermogram. The Differential Scanning Calorimeter (DSC) thermogram of Form A is substantially as depicted in FIG. 3. Crystalline Metaxalone Form A is bioavailable and has a $C_{max}$ value of 37.68±4.1 µg/ml. The $T_{max}$ value is 1.50±0.3 hr. The $AUC_{last}$ value of Form A is 324.78±110.4 hrµg/ml. It has a half-life value of 7.25±2.9 hr.

Bioavailable crystalline Form A of Metaxalone has an $AUC_{inf}$ value of 451.41±165.5 hrµg/ml, a $MRT_{last}$ value of 5.49±1.8 hr; and a $Cl_{obs}$ value of 369.84±127.3 ml/hr/kg.

The organic solvent used in the preparation of the Form A is selected from aliphatic, cyclic or aromatic substituted or unsubstituted hydrocarbons such as petroleum ether, hexane, heptane, cyclopentane, cyclohexane, benzene, toluene, xylene, nitrobenzene, or chlorobenzene; halogenated hydrocarbons such as chloroform, carbon tetrachloride, dichloromethane, or dichloroethane; carboxylic acid esters such as ethyl acetate, methyl acetate, or butyl acetate; ketones such as acetone, methylisobutylketone, methylethylketone, or cyclohexanone; cyclic and acyclic ethers such as ether, tetrahydrofuran, dioxan, or dimethoxyethane; polyethers such as poly (alkylene glycol)s; nitrites such as acetonitrile, or benzonitrile; amides such as dimethylformamide, or dimethylacetamide. Preferably, the solvent is selected from ethylacetate, acetonitrile or methyl ethyl ketone.

Preferably crystalline Form-A of Metaxalone of the invention exhibits an X-ray (powder) diffraction pattern having characteristic peaks at diffraction angles 2-θ of about 4.41, 13.34, and 17.86; an I.R spectrum with $v_{max}$ at about 1728 $cm^{-1}$ and 1738 $cm^{-1}$ for the carbonyl group; and an endotherm at about 122.33° C., in its Differential Scanning Calorimeter (DSC) thermogram.

The X-ray (powder) diffraction pattern is as depicted in FIG. 5; I.R spectrum is as depicted in FIG. 1; and Differential Scanning Calorimeter (DSC) thermogram is as depicted in FIG. 3.

Preferably, the crystalline Form-A of Metaxalone prepared according to the invention exhibits a $C_{max}$ value of 37.68±4.1 µg/ml; a $T_{max}$ value of 1.50±0.3 hr; an $AUC_{last}$ value of 324.78±110.4 hrµg/ml; an $AUC_{inf}$ value of 451.41±165.5 hrµg/ml; a half-life value of 7.25±2.9 hr; a $MRT_{last}$ value of 5.49±1.8 hr; and a $Cl_{obs}$ value of 369.84±127.3 ml/hr/kg.

Form B of Metaxalone

The crystalline Form B of Metaxalone has a X-ray (powder) diffraction pattern is substantially as depicted in FIG. 6. It exhibits an I.R spectrum with $v_{max}$ at about 1722 $cm^{-1}$ and 1753 $cm^{-1}$ for the carbonyl group, the I.R spectrum is substantially as depicted in FIG. 2.

Crystalline Form B exhibits an endotherm at about 121.5° C. and 122.48° C., in its Differential Scanning Calorimeter (DSC) thermogram. The Differential Scanning Calorimeter (DSC) thermogram is substantially as depicted in FIG. 4.

Crystalline Metaxalone Form B which is bioavailable and has a $C_{max}$ value of 40.73±2.8 μg/ml. The $T_{max}$ value is 2.08±1.4 hr. The Form B has an $AUC_{last}$ value of 333.32±159.9 hrμg/ml. It has a half-life value of 4.49±1.7 hr. The said Form B has $AUC_{inf}$ value of 389.07±200.6 hrμg/ml; a $MRT_{last}$ value of 5.50±1.8 hr; and a $Cl_{obs}$ value of 472.72±214.7 ml/hr/kg.

The organic solvent used in the process for preparation of Form B is selected from aliphatic, cyclic or aromatic substituted or unsubstituted hydrocarbons such as petroleum ether, hexane, heptane, cyclopentane, cyclohexane, benzene, toluene, xylene, nitrobenzene, or chlorobenzene; halogenated hydrocarbons such as chloroform, carbon tetrachloride, dichloromethane, or dichloroethane; carboxylic acid esters such as ethyl acetate, methyl acetate, or butyl acetate; ketones such as acetone, methylisobutylketone, methylethylketone, or cyclohexanone; cyclic and acyclic ethers such as ether, tetrahydrofuran, dioxan, or dimethoxyethane; polyethers such as poly(alkylene glycol)s; nitriles such as acetonitrile, or benzonitrile; amides such as dimethylformamide, or dimethylacetamide. The preferred solvent is selected from ethylacetate, acetonitrile or methyl ethyl ketone.

The crystalline Form-B of Metaxalone exhibits an X-ray (powder) diffraction pattern having characteristic peaks at diffraction angles 2-θ of about 10.26, 14.18, 19.0 and 22.4; an I.R spectrum with $v_{max}$ at about 1722 cm$^{-1}$ and 1753 cm$^{-1}$ for the carbonyl group; and an endotherm at about 121.5° C. and 122.48° C., in its Differential Scanning Calorimeter (DSC) thermogram.

Pharmaceutical Compositions

Pharmaceutical composition according to the invention comprise crystalline Form A or Form B of Metaxalone and pharmaceutically acceptable excipients. The pharmaceutical compositions are particularly suitable for oral administration especially in the form of a tablet, a capsule, or a suspension useful for the treatment of discomforts associated with acute, painful musculoskeletal conditions.

The excipients are selected from disintegrants, fillers, binders, surfactants and lubricants.

The disintegrant is selected from alginic acid, carboxymethylcellulose calcium, carboxymethylcellulose sodium, colloidal silicon dioxide, croscarmellose sodium, crospovidone, guar gum, magnesium aluminum silicate, methylcellulose, microcrystalline cellulose, polyacrilin potassium, powdered cellulose, pregelatinized starch, sodium or calcium alginate and starch.

The filler is selected from calcium carbonate, calcium sulfate, compressible sugars, confectioner's sugar, dextrates, dextrin, dextrose, dibasic calcium phosphate dihydrate, glyceryl palmitostearate, hydrogenated vegetable oil (type I), kaolin, lactose, magnesium carbonate, magnesium oxide, maltodextrin, mannitol, polymethacrylates, potassium chloride, powdered cellulose, pregelatinized starch, sodium chloride, sorbitol, starch, sucrose, sugar spheres, talc and tribasic calcium phosphate.

The binder is selected from acacia, alginic acid, carbomer, carboxymethylcellulose sodium, dextrin, ethylcellulose, gelatin, guar gum, hydrogenated vegetable oil (type I), hydroxyethyl cellulose, hydroxypropyl cellulose, hydroxypropyl methylcellulose, liquid glucose, magnesium aluminum silicate, maltodextrin, methylcellulose, polymethacrylates, povidone, pregelatinized starch, sodium alginate, corn starch, and zein.

The surfactant is selected from anionic and cationic surfactants, such as sodium lauryl sulfate, docusate sodium (dioctyl sulfosuccinate sodium salt), benzalkonium chloride, benzethonium chloride, and cetrimide (alkyltrimethylammonium bromide).

The lubricant is selected from stearate acid metal salt (magnesium stearate or calcium stearate), stearic acid, sodium lauryl sulfate, sodium lauryl magnesium, powdered gum arabic, carnauba wax, anhydrous silicic acid, magnesium oxide, silic acid hydrate, boric acid, fatty acid sodium salt and leucine.

A particularly clear distinction in the two crystalline forms can be seen by their respective Infrared Spectra, Differential Scanning Calorimetric (DSC) Thermogram and X-ray (powder) diffraction patterns.

In a DSC Thermogram, Form A crystals exhibit a single melting endotherm at about 122.33° C., whereas Form B crystals exhibit two melting endotherms at about 121.5° C. and 122.48° C. These are summarized in FIG. 3 and FIG. 4 respectively.

TABLE I

X-Ray (powder) Diffraction Pattern Values of Crystalline Form A Metaxalone

| Angle (°2θ) | d-value (A°) | Intensity (%) |
|---|---|---|
| 4.410 | 20.01994 | 100 |
| 8.870 | 9.96107 | 5.5 |
| 13.343 | 6.63044 | 15.8 |
| 15.907 | 5.56698 | 0.5 |
| 16.596 | 5.33754 | 1.6 |
| 17.148 | 5.16674 | 0.4 |
| 17.862 | 4.96172 | 10.2 |
| 18.371 | 4.82550 | 2.8 |
| 19.158 | 4.62905 | 0.4 |
| 20.659 | 4.29595 | 1.3 |
| 21.048 | 4.21738 | 0.5 |
| 22.387 | 3.96808 | 2.7 |
| 22.812 | 3.89515 | 4.4 |
| 23.408 | 3.79726 | 0.9 |
| 24.083 | 3.69232 | 0.9 |
| 24.851 | 3.57990 | 1.2 |
| 25.481 | 3.49290 | 0.9 |
| 26.076 | 3.41451 | 4.5 |
| 26.926 | 3.30856 | 2.6 |
| 27.400 | 3.25243 | 0.6 |
| 28.316 | 3.14922 | 0.3 |
| 29.677 | 3.00784 | 0.8 |
| 31.582 | 2.83067 | 2.6 |
| 34.416 | 2.60376 | 0.3 |
| 36.249 | 2.47622 | 1.3 |
| 42.728 | 2.11452 | 0.8 |
| 44.038 | 2.05460 | 0.3 |

TABLE II

X-Ray (powder) Diffraction Pattern Values of Crystalline Form B Metaxalone

| Angle (°2θ) | d-value (°A) | Intensity (%) |
|---|---|---|
| 10.261 | 8.61422 | 100.0 |
| 11.244 | 7.86292 | 4.4 |
| 14.189 | 6.23687 | 25.0 |
| 15.696 | 5.64131 | 4.2 |
| 16.275 | 5.44197 | 1.0 |
| 16.643 | 5.32239 | 2.5 |
| 17.294 | 5.12360 | 5.9 |
| 18.550 | 4.77930 | 18.5 |
| 19.009 | 4.66497 | 26.7 |
| 19.499 | 4.54890 | 0.8 |
| 20.723 | 4.28280 | 18.3 |

TABLE II-continued

X-Ray (powder) Diffraction Pattern Values of Crystalline Form B Metaxalone

| Angle (°2θ) | d-value (°A) | Intensity (%) |
|---|---|---|
| 21.593 | 4.11209 | 14.8 |
| 22.404 | 3.96508 | 22.1 |
| 23.768 | 3.74063 | 4.0 |
| 24.529 | 3.62615 | 14.0 |
| 25.238 | 3.52594 | 5.6 |
| 25.759 | 3.45585 | 11.3 |
| 26.442 | 3.36811 | 4.0 |
| 27.076 | 3.29066 | 7.2 |
| 27.699 | 3.21796 | 3.1 |
| 28.176 | 3.16463 | 1.9 |
| 29.668 | 3.00878 | 6.6 |
| 29.989 | 2.97733 | 6.2 |
| 30.850 | 2.89609 | 1.6 |
| 31.613 | 2.82793 | 2.8 |
| 32.693 | 2.77245 | 1.1 |
| 34.240 | 2.61675 | 1.2 |
| 35.432 | 2.53142 | 1.3 |
| 37.028 | 2.42586 | 3.7 |
| 37.511 | 2.39574 | 1.9 |

Further, when these two forms were viewed microscopically, the crystals of Form-A were found to be cubical in shape whereas that of Form-B were found to be fine needles.

The essential differences between Form A and Form B crystals of Metaxalone of the present invention are summarized in Table-III.

TABLE III

The Essential Differences between Crystalline Form-A and Form-B of Metaxalone

| Distinctions | Polymorph A | Polymorph B |
|---|---|---|
| IR Spectrum (Carbonyl stretching, $\nu_{max}$ (cm$^{-1}$) | 1728 1738 | 1753 1722 |
| DSC Thermogram (° C.) | 122.33 | 121.5 (Ist Endotherm) 122.48 (2$^{nd}$ Endotherm) |
| X-Ray (powder) Diffractions Pattern (2θ) | 4.41, 13.34, and 17.86 | 10.26, 14.18, 19.0 and 22.4 |
| Shape | Cubical | Needle |
| Process | Rapid cooling from solvents | Slow cooling from solvents |

Furthermore, based on pharmacokinetic studies, in female wistar rats it was found that oral administration of a test formulation of both form-A and form-B crystals of Metaxalone at a dose of 150 mg/kg body weight of the rats results in a mean $C_{max}$ (Mean concentration of drug in blood plasma) of 37.68±4.1 μg/ml for crystalline form A crystals and 40.73±2.8 for crystalline form B crystals of Metaxalone.

Besides, the $C_{max}$ values, the pharmacokinetic studies also determined other characteristic profiles of the two crystalline forms. For the form A crystals, it was found to have a $T_{max}$ of 1.50±0.3 hr, $AUC_{last}$ of 324.78±110.4 hr μg/ml and $AUC_{inf}$ of 451.41±165.5 hrμg/ml. For the form B crystals, it was found to have $T_{max}$ of 2.08±1.4 hr, $AUC_{last}$ of 333.32±159.9 hr μg/ml and $AUC_{inf}$ of 389.07±200.6 hrμg/ml.

Based on the observed $C_{max}$ values for the two crystalline forms it could be understood that both the crystalline forms (Form A and Form B crystals) are bioavailable.

A comparison of the pharmacokinetic profiles of the two crystalline forms A and B are summarized in Table-IV.

TABLE IV

Comparison of the Pharmacokinetic Profiles of the two Crystalline Forms A and B of Metaxalone

| | | Estimate Mean (Mean ± SD) | |
|---|---|---|---|
| Parameter | Units | Metaxalone- Form A | Metaxalone- Form B |
| Lambda z | 1/hr | 0.119 ± 0.07 | 0.172 ± 0.05 |
| Half Life | hr | 7.25 ± 2.9 | 4.49 ± 1.7 |
| $T_{max}$ | hr | 1.50 ± 0.3 | 2.08 ± 1.4 |
| $C_{max}$ | μg/ml | 37.68 ± 4.1 | 40.73 ± 2.8 |
| $AUC_{last}$ | hrμg/ml | 324.78 ± 110.4 | 333.32 ± 159.9 |
| $AUC_{inf}$ | hrμg/ml | 451.41 ± 165.5 | 389.07 ± 200.6 |
| $Vz_{obs}$ | ml/kg | 3466.02 ± 978.8 | 2654.18 ± 422.2 |
| $Cl_{obs}$ | ml/hr/kg | 369.84 ± 127.3 | 472.72 ± 214.7 |
| $MRT_{last}$ | hr | 5.49 ± 1.8 | 5.50 ± 1.8 |

DETAILED DESCRIPTION OF THE INVENTION

The present invention is as detailed hereinunder.

A) Preparation of Form A Crystals of Metaxalone

As mentioned hereinearlier, Form A crystals of Metaxalone can be prepared through "rapid cooling" to ambient temperature a hot solution of Metaxalone in an organic solvent or mixtures thereof and collecting the crystals.

More specifically, Form A crystals can be obtained by rapid cooling a hot solution of Metaxalone in an organic solvent to ambient temperature over a period of between 1 to 1.5 hours.

The Metaxalone that can be used for preparation of Form A crystals can be any of those prepared by the methods of U.S. Pat. No. 3,062,827, WO03061552, U.S. Pat. No. 3,446,814 or U.S. Pat. No. 6,562,980.

The organic solvents that can be used for the preparation of the Form A crystals of the present invention are those routinely utilized in drug manufacturing processes. Such organic solvents include, but are not limited to aliphatic, cyclic or aromatic substituted or unsubstituted hydrocarbons such as petroleum ether, hexane, heptane, cyclopentane, cyclohexane, benzene, toluene, xylene, nitrobenzene, chlorobenzene etc; halogenated hydrocarbons such as chloroform, carbon tetrachloride, dichloromethane, dichloroethane etc; carboxylic acid esters such as ethyl acetate, methyl acetate, butyl acetate etc; ketones such as acetone, methylisobutylketone, methylethylketone, cyclohexanone etc; cyclic and acyclic ethers such as ether, tetrahydrofuiran, dioxan, dimethoxyethane etc; polyethers such as poly(alkylene glycol)s; nitriles such as acetonitrile, benzonitrile etc; amides such as dimethylformamide, dimethylacetamide etc.

Of all these solvents, carboxylic acid esters are preferred and among the carboxylic acid esters, ethyl acetate is the most preferred solvent.

The solvent is employed in a proportion, which would be sufficient to dissolve Metaxalone at the boiling point of the solvent or mixtures of the solvent used.

In a typical embodiment, Metaxalone is added to any of the above-mentioned organic solvent or mixtures thereof, kept at a temperature of between 40-80° C. and further heated to reflux to obtain a clear solution. The solution is then cooled to a temperature of between 20-35° C. within 90 mins and is further cooled to a lower temperature, say between 0-10° C., from which the crystallized Metaxalone-Form A can be collected by filtration and drying.

In a specific embodiment, Metaxalone is dissolved in ethyl acetate at a temperature of between 40-80° C. and then heated to reflux to obtain a clear solution. The solution is then cooled to a temperature of between 20-35° C. over a period of between 1 to 1.5 hours and further cooled to a lower temperature between 0-10° C. Crystals of Metaxalone Form A obtained are filtered and dried.

Figure 1:
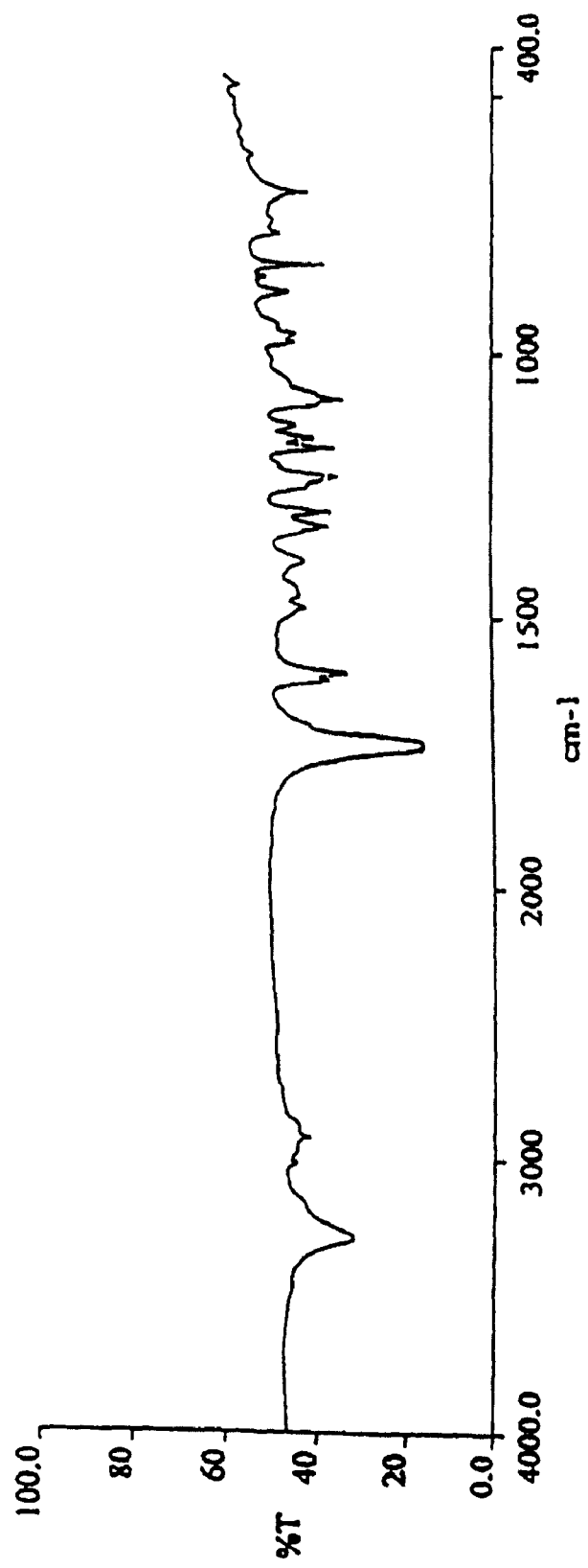
FIG. 1 represents the IR-Spectrum of Crystalline Form A of Metaxalone.
Figure 3:
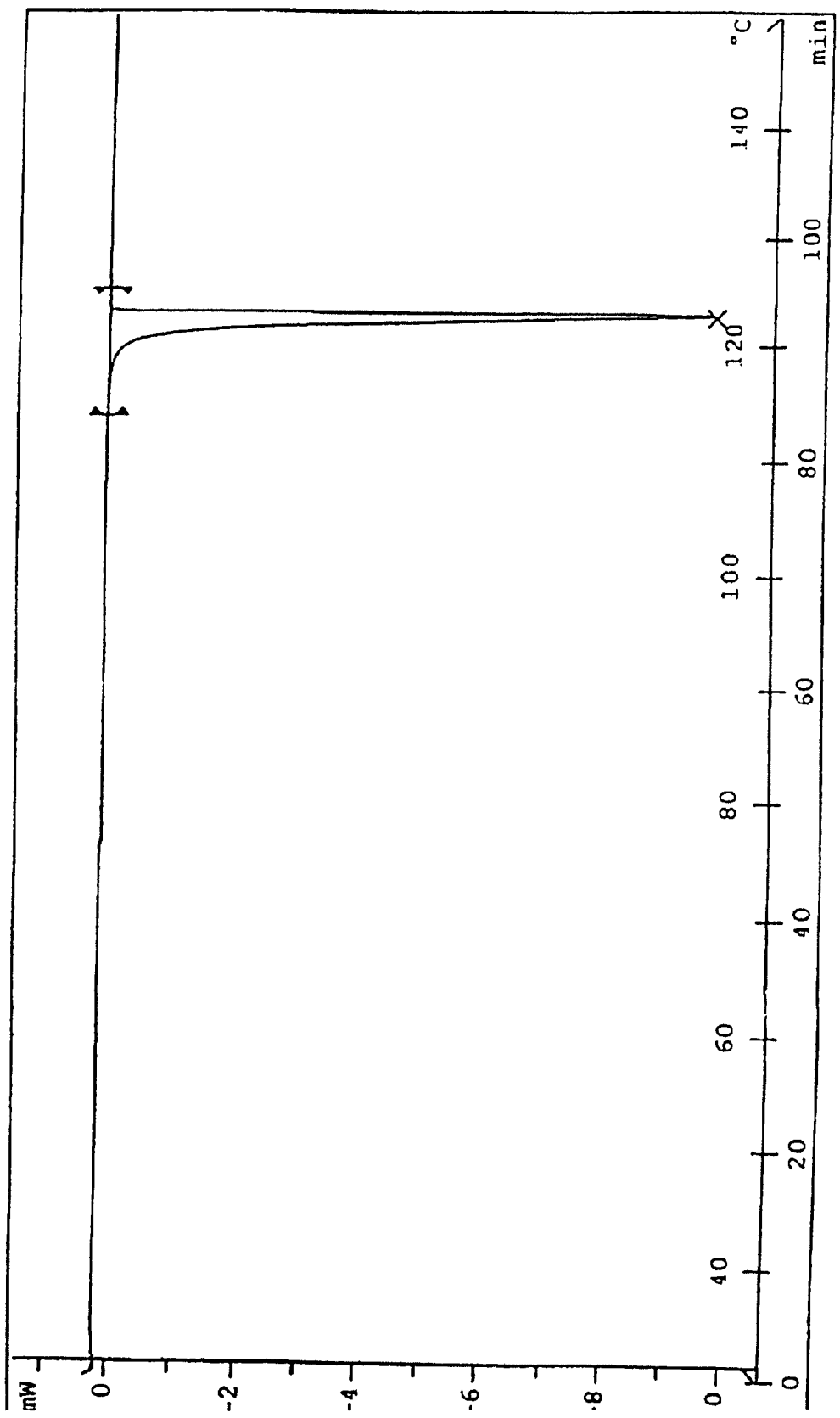
FIG. 3 represents the DSC Thermogram of Crystalline Form A of Metaxalone.
Figure 5:
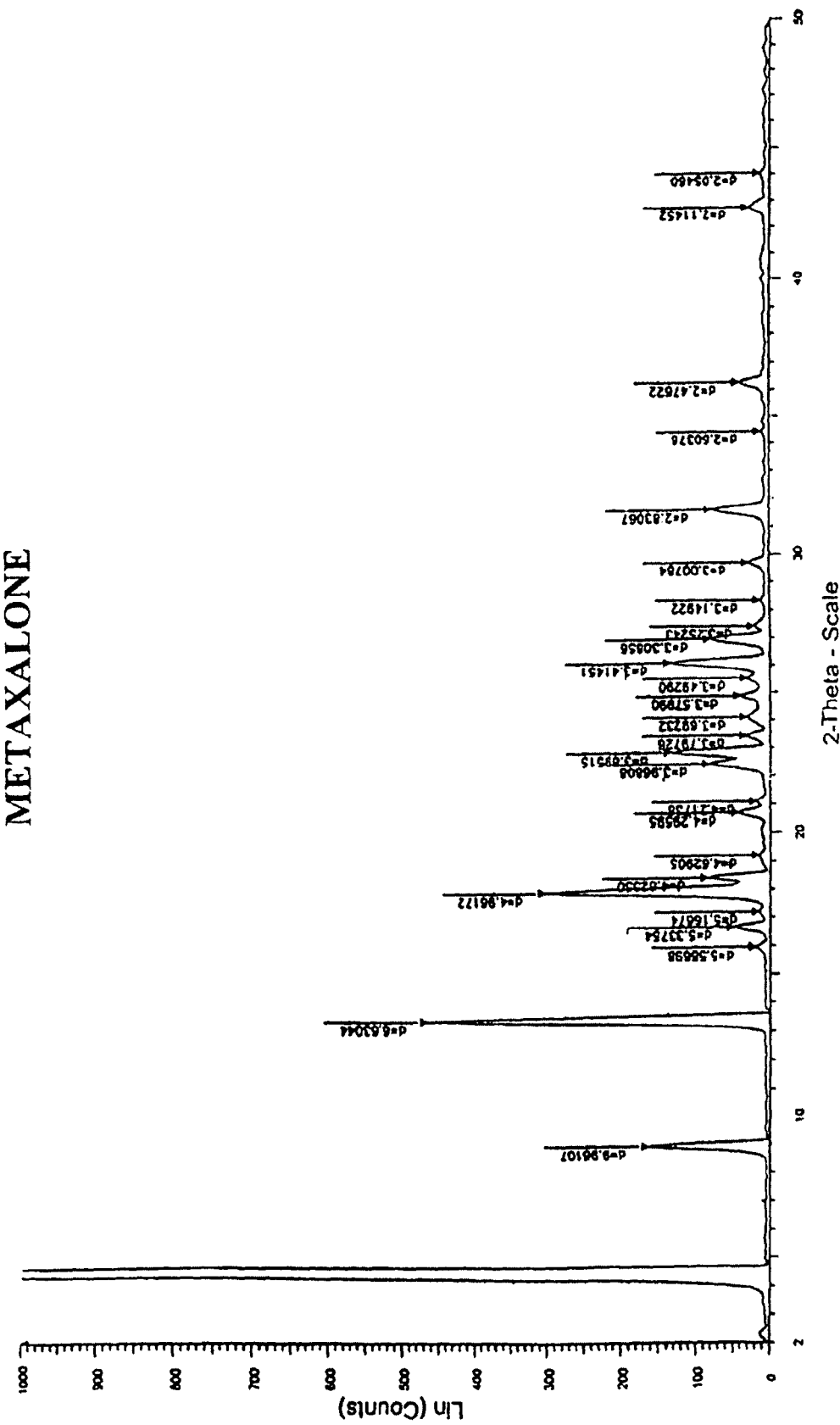
FIG. 5 represents the X-Ray (powder) Diffraction pattern of Crystalline Form A of Metaxalone.

The crystals of Form A Metaxalone thus obtained are cubical in shape, and exhibit the characteristic I.R Spectra as given in FIG. 1, DSC Thermogram as given in FIG. 3, and X-Ray (powder) Diffraction as given in FIG. 5 and Table-I.

B) Preparation of Form B Crystals of Metaxalone

Form-B crystals of Metaxalone can be prepared by "slow cooling" to ambient temperature a hot solution of Metaxalone in an organic solvent or mixtures thereof and collecting the crystals.

More specifically, Form B crystals can be obtained by slow cooling a hot solution of Metaxalone in an organic solvent to ambient temperature over a period of time exceeding 1.5 hours.

The Metaxalone molecule for the preparation of Form B crystals can be prepared by any of the methods, mentioned in the above-identified patents.

The organic solvents that can be used for the preparation of the Form B crystals of the present invention are also those that are routinely utilized in drug manufacturing processes. Such organic solvents include, but are not limited to aliphatic, cyclic or aromatic substituted or unsubstituted hydrocarbons such as petroleum ether, hexane, heptane, cyclopentane, cyclohexane, benzene, toluene, xylene, nitrobenzene, chlorobenzene etc; halogenated hydrocarbons such as chloroform, carbon tetrachloride, dichloromethane, dichloroethane, etc; carboxylic acid esters such as ethyl acetate, methyl acetate, butyl acetate etc; ketones such as acetone, methylisobutylketone, methylethylketone, cyclohexanone etc; cyclic and acyclic ethers such as ether, tetrahydrofuran, dioxan, dimethoxyethane etc; polyethers such as poly(alkylene glycol)s; nitriles such as acetonitrile, benzonitrile; amides such as dimethylformamide, dimethylacetamide etc.

Of all these solvents, carboxylic acid esters are preferred and among the carboxylic acid esters, ethyl acetate is the most preferred solvent.

In a typical embodiment, Metaxalone is added to any of the above-mentioned organic solvent or mixtures thereof, kept at a temperature of between 40-80° C. and further heated to reflux to obtain a clear solution. The solution is then slowly cooled to a temperature of between 20-35° C. for a period over 90 min and is further cooled to a lower temperature, say between 0-10° C., from which the crystallized Metaxalone-Form B can be collected by filtration and dried.

In a specific embodiment, Metaxalone is dissolved in ethyl acetate at a temperature of between 40-80° C. and then heated to reflux to obtain a clear solution. The solution is then cooled to a temperature of between 20-35° C. for a period of time exceeding 1.5 hours and is further cooled to a lower temperature between 0-10° C. Fine crystals of Metaxalone Form B obtained are filtered and dried.

Figure 2:
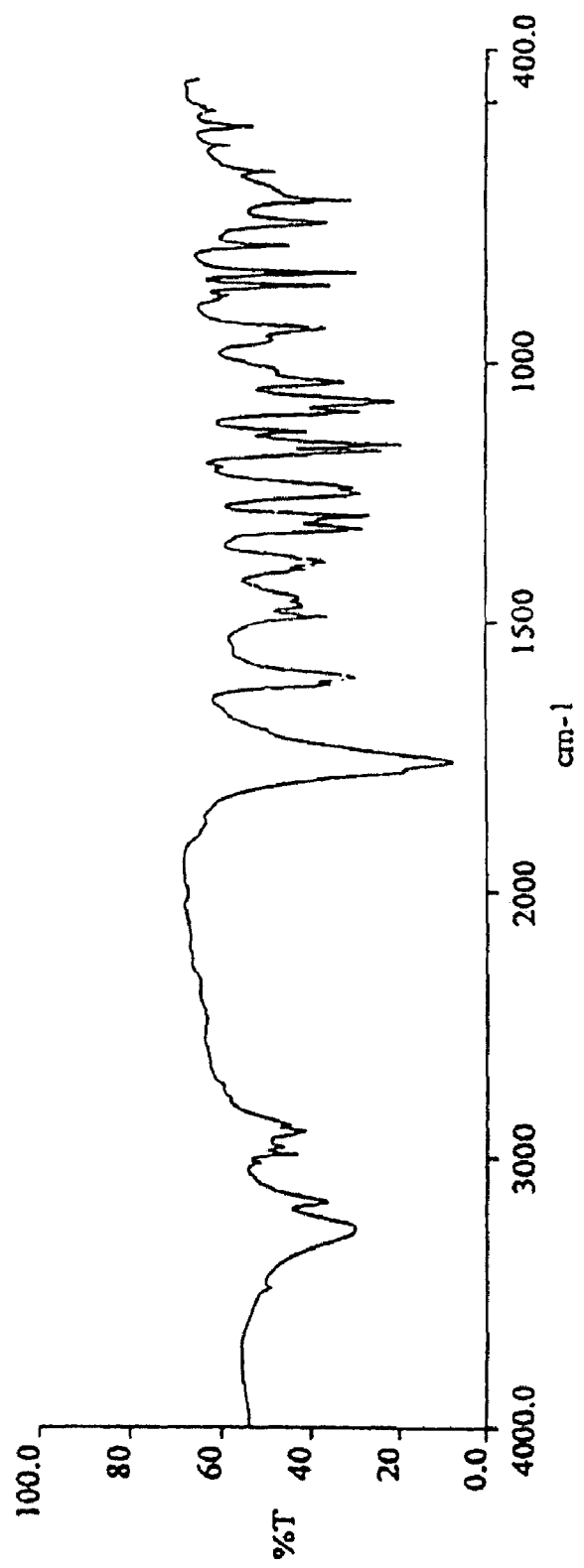
FIG. 2 represents the IR-Spectrum of Crystalline Form B of Metaxalone.
Figure 4:
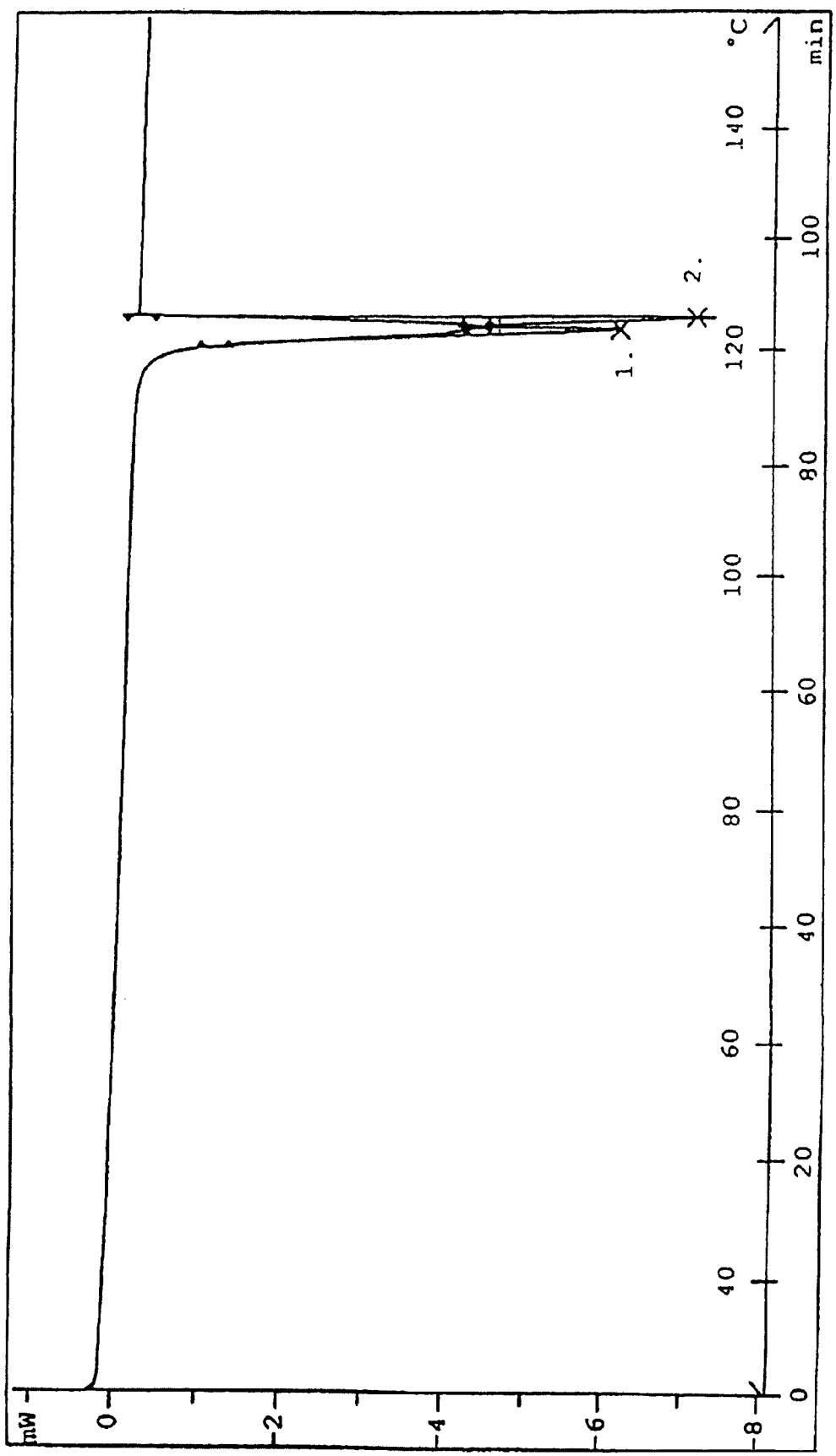
FIG. 4 represents the DSC Thermogram of Crystalline Form B of Metaxalone.
Figure 6:
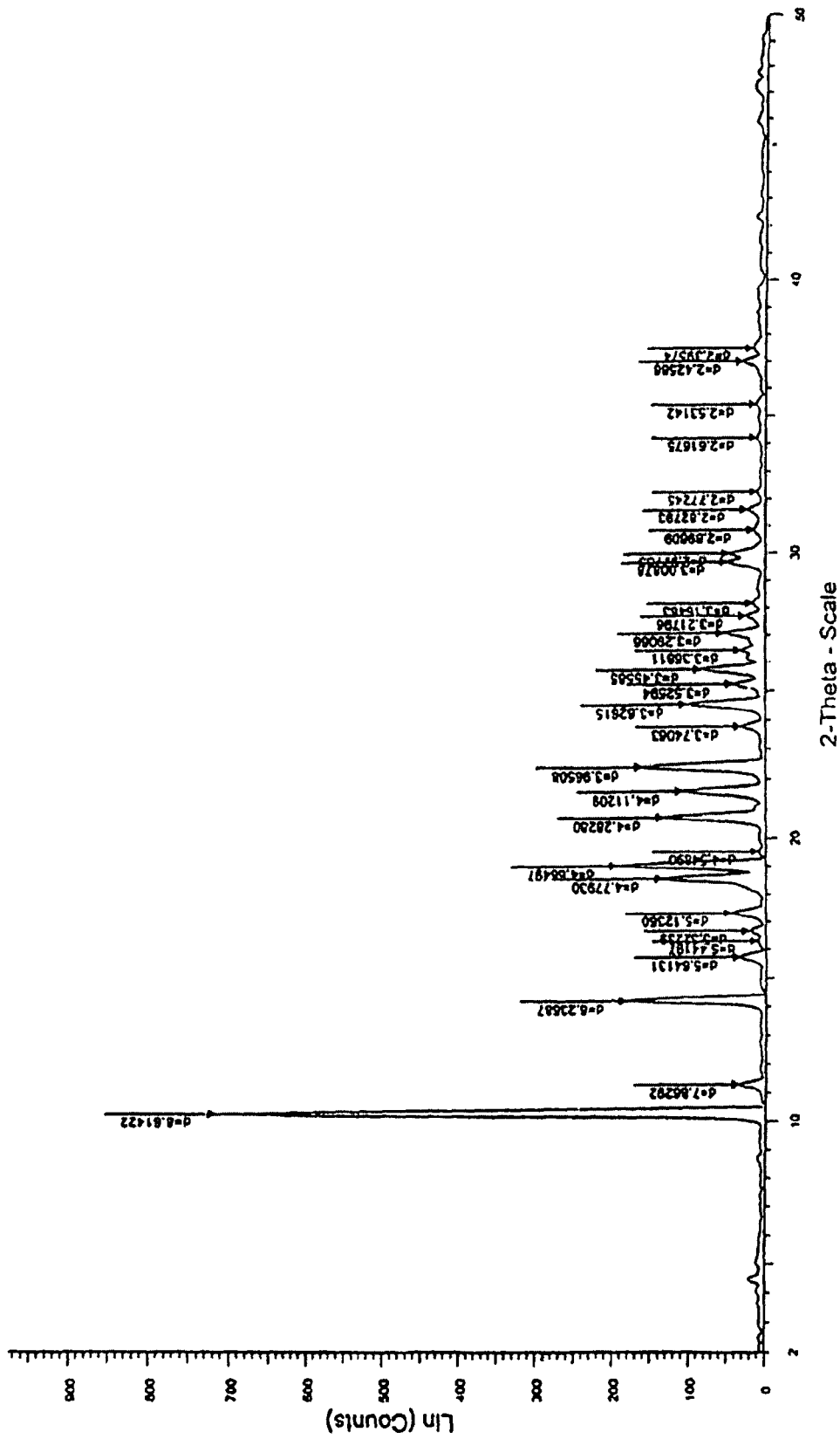
FIG. 6 represents the X-Ray (powder) Diffraction pattern of Crystalline Form B of Metaxalone.
Figure 7:
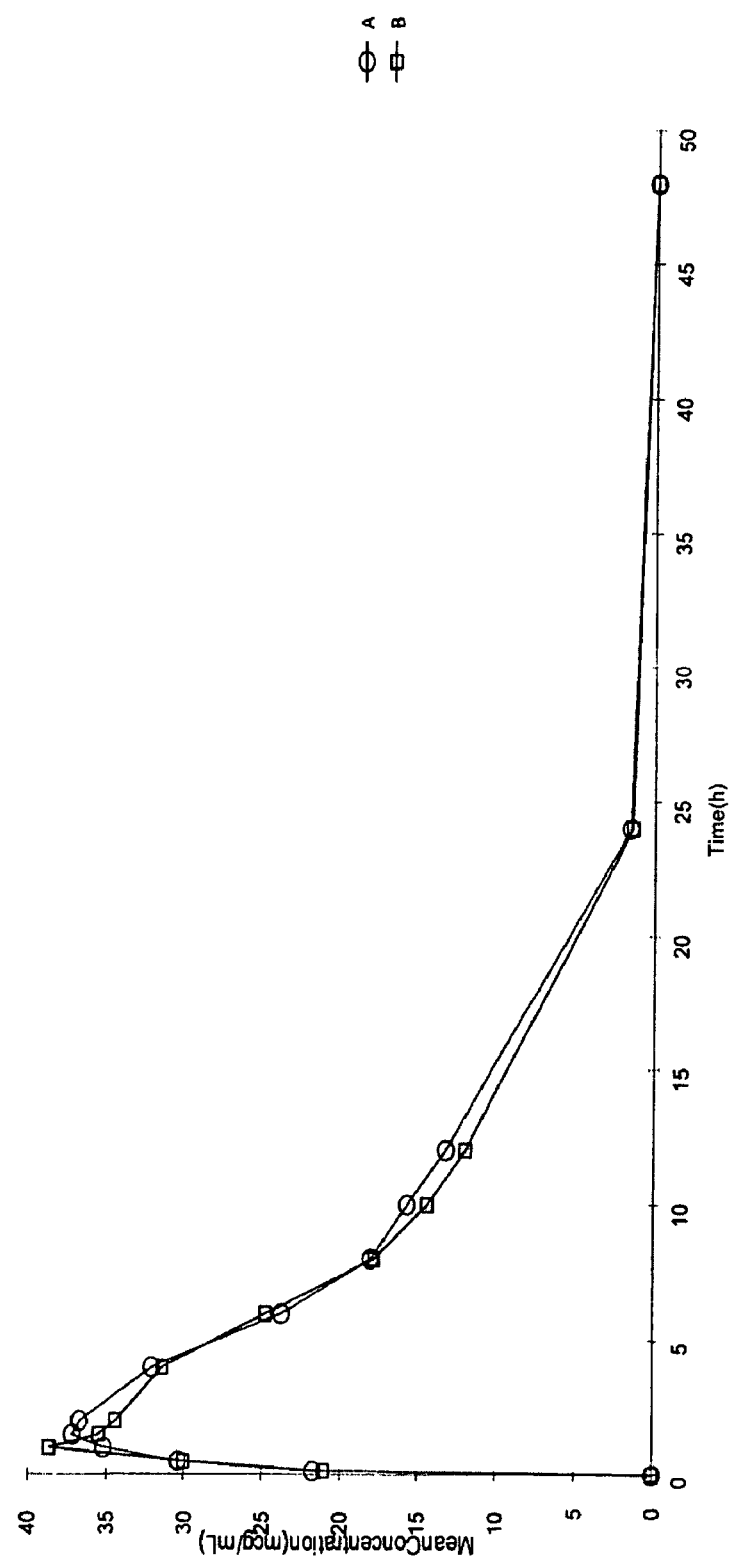
FIG. 7 represents mean plot concentration v/s time of Metaxalone Form A and Form B crystals in female Wistar rats at an oral dose of 150 mg/kg.
Figure 8:
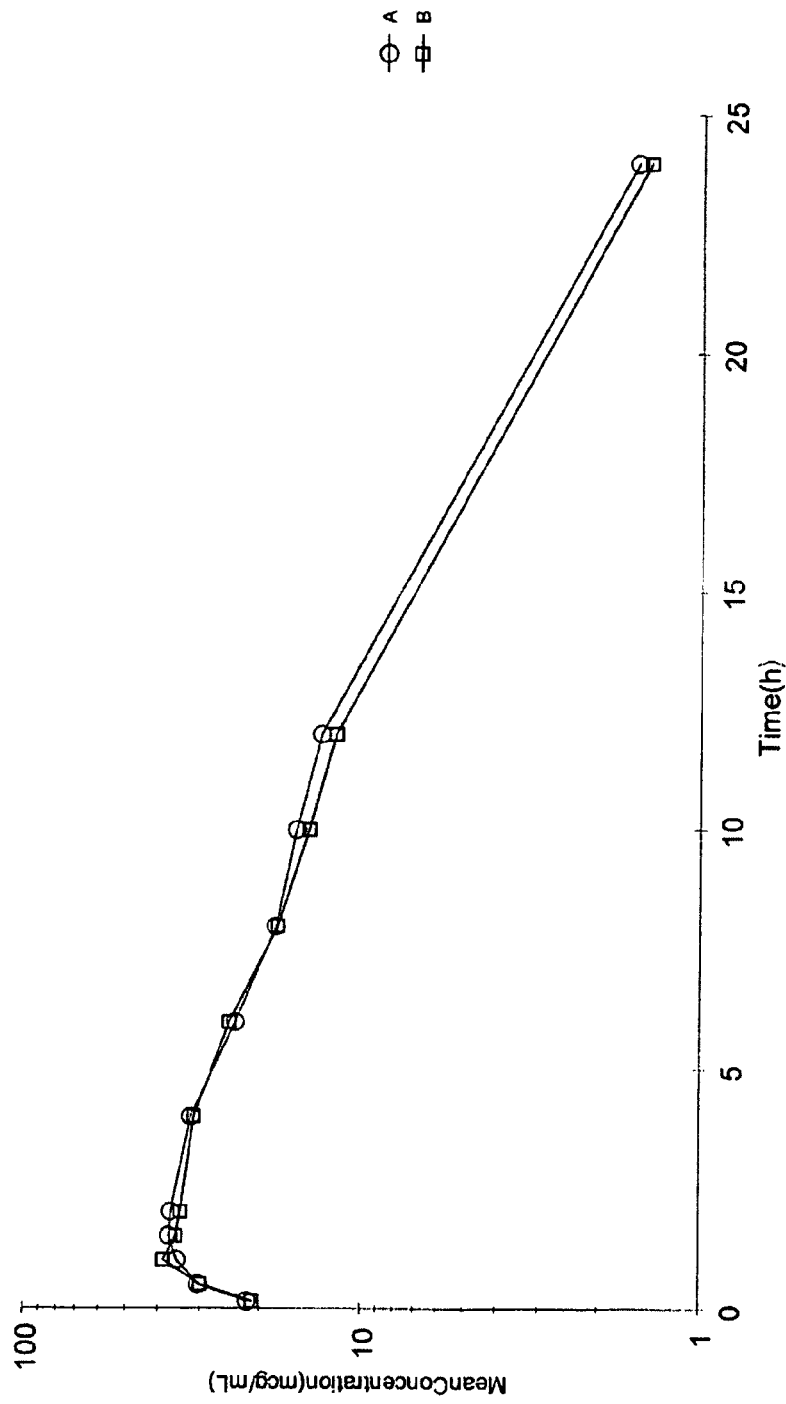
FIG. 8 represents semi logarithmic mean plot concentration v/s time of Metaxalone Form A and Form B crystals in female Wistar rats at an oral dose of 150 mg/kg.

The Form B Metaxalone obtained, exhibits the characteristic I.R Spectra as given in FIG. 2, DSC Thermogram as given in FIG. 4, and X-Ray (powder) Diffraction as given in Table 2 and FIG. 6.

C) Bioavailability Studies on Crystalline Form A and B of Metaxalone

A study was undertaken to compare the bioavailability and pharmacokinetic profile of the two crystalline Forms A and B of metaxalone in female wistar rat under fasting condition. A suspension of metaxalone form A and Form B having a concentration of 15.0 mg/ml was prepared using 0.1% Tween-80 in 0.25% carboxy methyl cellulose (CMC). The formulation was used for dosing as such without any further dilution.

Twelve rats were taken, out of which six rats were administered form A crystals of Metaxalone and other six rats were adminstered form B crystals of Metaxalone, in different injection volumes based on body weight, resulting in dose of 150 mg/kg. A total thirteen (0.6 ml) blood samples were collected from each rat into prelabeled tubes containing EDTA solution, by retro-orbital bleeding under mild ether anesthesia. The blood samples were withdrawn at time points of 0 (prior to dosing), 15, 30 mins, 1, 1.5, 2.0, 4.0, 6.0, 8.0, 10.0, 12.0, 24 and 48 hrs post administration. The samples were centrifuged at 4000 rpm for 10 mins at room temperature. Seperated plasma samples were transferred into prelabeled tubes and stored upright in cyrobox. These cyroboxes were then transfered into a deep freezer maintained at −20° C. for the final storage until the completion of analysis.

HPLC system of Shimadzu LC—2010$C_{HT}$ series equipped with shimadzu UV-VIS detector, analytical column YMC Pack ODS C-18, 5 μm, (150×4.6 mm) and a data acquisition system (LC solution software) were used for the quantitative determination of metaxalone in rat plasma.

The results were plotted using the conventional AUC method to calculate pharmacokinetic ters ($C_{max}$, $T_{max}$ and AUC (area under the curve, a measure of total bioavailability). The pharmacokinetic results for the crystalline form A and B are summarized in Table-V

TABLE V

Pharmacokinetic Parameters of Metaxalone Crystalline Form A and Form-B in female wistar rat at oral dose of 150 mg/kg

| | $T_{max}$ Form | | $C_{max}$ Form | | | $AUC_t$ Form | | | $AUC_{in}$ Form | | |
|---|---|---|---|---|---|---|---|---|---|---|---|
| Rat | A | B | A | B | A/B % | A | B | A/B % | A | B | A/B % |
| 1 | 1.50 | 1.00 | 39.57 | 38.16 | 103.7 | 530.31 | 207.73 | 255.3 | 667.12 | 229.04 | 291.3 |
| 2 | 1.50 | 1.50 | 31.90 | 37.54 | 85.0 | 251.62 | 285.51 | 88.1 | 348.88 | 288.56 | 120.9 |
| 3 | 1.50 | 1.00 | 43.08 | 38.75 | 111.2 | 371.39 | 188.83 | 196.7 | 646.72 | 196.86 | 328.5 |
| 4 | 2.00 | 1.00 | 33.77 | 43.65 | 77.4 | 259.03 | 306.89 | 84.4 | 398.52 | 360.78 | 110.5 |
| 5 | 1.50 | 4.00 | 38.46 | 43.04 | 89.4 | 283.70 | 384.99 | 73.7 | 380.50 | 551.70 | 69.0 |
| 6 | 1.00 | 4.00 | 39.32 | 43.27 | 90.9 | 252.67 | 626.04 | 40.4 | 267.03 | 707.50 | 37.7 |
| N | 6 | 6 | 6 | 6 | | 6 | 6 | | 6 | 6 | |
| Mean | 1.500 | 2.083 | 37.683 | 40.735 | | 324.786 | 333.329 | | 451.461 | 389.072 | |
| SD | 0.316 | 1.497 | 4.116 | 2.864 | | 110.433 | 159.994 | | 165.536 | 200.649 | |
| Min | 1.00 | 1.00 | 31.90 | 37.54 | | 251.62 | 188.83 | | 267.03 | 196.86 | |
| Max | 2.00 | 4.00 | 43.08 | 43.65 | | 530.31 | 626.04 | | 667.12 | 707.50 | |
| CV % | 21.1 | 71.9 | 10.9 | 7.0 | | 34.0 | 48.0 | | 36.7 | 51.6 | |

The pharmacokinetic studies also determined other characteristic profiles of the two crystalline forms. For the form A crystals, it was found to have a $C_{max}$ of 37.68±4.1 µg/ml $T_{max}$ of 1.50±0.3 hr, $AUC_{last}$ of 324.78±110.4 hr·µg/ml $AUC_{inf}$ of 451.41±165.5 hr·µg/ml and $MRT_{last}$ of 5.49±1.8

For the form B crystals, it was found to have $C_{max}$ of 40.73±2.8 µg/ml $T_{max}$ of 2.08±1.4 hr, $AUC_{last}$ of 333.32±159.9 hr·µg/ml. $AUC_{inf}$ of 389.07±200.6 hr·µg/ml and $MRT_{last}$ of 5.50±1.8.

The various pharmacokinetic parameters of Form-A and Form-B are summarized in the Table IV

TABLE IV

Comparison of the Pharmacokinetic Profiles of the Two Crystalline Forms A and B

| | | Estimate Mean (Mean ± SD) | |
|---|---|---|---|
| Parameter | Units | Metaxalone- Form A | Metaxalone- Form B |
| Lambda z | 1/hr | 0.119 ± 0.07 | 0.172 ± 0.05 |
| Half Life | hr | 7.25 ± 2.9 | 4.49 ± 1.7 |
| $T_{max}$ | hr | 1.50 ± 0.3 | 2.08 ± 1.4 |
| $C_{max}$ | µg/ml | 37.68 ± 4.1 | 40.73 ± 2.8 |
| $AUC_{last}$ | hr * µg/ml | 324.78 ± 110.4 | 333.32 ± 159.9 |
| $AUC_{inf}$ | hr * µg/ml | 451.41 ± 165.5 | 389.07 ± 200.6 |
| $Vz_{obs}$ | ml/kg | 3466.02 ± 978.8 | 2654.18 ± 422.2 |
| $Cl_{obs}$ | ml/hr/kg | 369.84 ± 127.3 | 472.72 ± 214.7 |
| $MRT_{last}$ | hr | 5.49 ± 1.8 | 5.50 ± 1.8 |

D) Pharmaceutical Compositions of Crystalline Form A and B of Metaxalone

The Metaxalone form-A and B crystals thus prepared can be formulated into pharmaceutical compositions for oral administration such as in the form of tablets, capsules, suspensions etc. More particularly, the crystalline forms of the present invention can be formulated into tablet dosage form by combination with appropriate pharmaceutically acceptable carriers or diluents, disintegrants, fillers, binders, surfactants and lubricants etc.

Examples of disintegrants include alginic acid, carboxymethylcellulose calcium, carboxymethylcellulose sodium, colloidal silicon dioxide, croscarmellose sodium, crospovidone, guar gum, magnesium aluminum silicate, methylcellulose, microcrystalline cellulose, polyacrilin potassium, powdered cellulose, pregelatinized starch, sodium or calcium alginate and starch.

Examples of fillers (also referred to as a diluent) include: calcium carbonate, calcium sulfate, compressible sugars, confectioner's sugar, dextrates, dextrin, dextrose, dibasic calcium phosphate dihydrate, glyceryl palmitostearate, hydrogenated vegetable oil (type I), kaolin, lactose, magnesium carbonate, magnesium oxide, maltodextrin, mannitol, polymethacrylates, potassium chloride, powdered cellulose, pregelatinized starch, sodium chloride, sorbitol, starch, sucrose, sugar spheres, talc and tribasic calcium phosphate.

Examples of binders include: acacia, alginic acid, carbomer, carboxymethylcellulose sodium, dextrin, ethylcellulose, gelatin, guar gum, hydrogenated vegetable oil (type I), hydroxyethyl cellulose, hydroxypropyl cellulose, hydroxypropyl methylcellulose, liquid glucose, magnesium aluminaum silicate, maltodextrin, methylcellulose, polymethacrylates, povidone, pregelatinized starch, sodium alginate, corn starch, and zein etc.

Examples of surfactants comprise anionic and cationic surfactants, such as sodium lauryl sulfate, docusate sodium (dioctyl sulfosuccinate sodium salt), benzalkonium chloride, benzethonium chloride, and cetrimide (alkyltrimethylammonium bromide).

Several kinds of lubricants can be used for tablet production method of the present invention. The type of lubricant is not specifically limited, for example, there are stearate acid metal salt (magnesium stearate, calcium stearate and so on), stearic acid, sodium lauryl sulfate, sodium lauryl magnesium, powdered gum arabic, carnauba wax, anhydrous silicic acid, magnesium oxide, silic acid hydrate, boric acid, fatty acid sodium salt, leucine, and so on which have been commonly used. One of them may be used solely or more than two of them may be combined.

Examples of solvent comprise water, ethanol or mixtures thereof.

The tablets of this invention can be prepared by conventional tablet forming techniques such as, for example, wet granulation and dry granulation. In the wet granulation process, the active ingredient or ingredients are mixed with some or all of the filler. This blend is then wet granulated with a solution of a binder in solvent. The resultant wet granulation is then dried and milled. The granules are then mixed with the remaining ingredients, which will include the lubricant, to produce the final mix, which is then compressed into tablets.

In the dry granulation process, the active ingredient or ingredients are mixed with the other ingredients without addition of any solvent, and thus without the need for drying. Again the final mix is compressed into tablets. The dry granulation approach is preferred as it is simpler and thus less costly.

Such pharmaceutical compositions are particularly useful for the treatment of pain and discomfort caused by strains, sprains and other muscle injuries in humans and animals.

The present invention is further illustrated by the following examples, which should not be construed as limiting the scope of the invention.

Example 1

Preparation of Metaxalone 3,5 dimethyl phenol or m-Xylenol (190 kg), Triglycidyl isocyanurate (150 kg), MIBK (500.0 Lt) and Potassium Hydroxide (7.5 kg) were charged to a reactor at room temperature. The temperature of the mixture was raised to 115-120° C. and thereafter the reaction mixture was agitated at this temperature for 3-4 hrs till the completion of the reaction. The reaction mixture was cooled to 0-5° C. and the precipitated solid was centrifuged and dried to give 270 kg (of Metaxalone) having purity of between 95-96%, as an off-white solid. 150 kg of Metaxalone, thus obtained was dissolved in chloroform (600 lit) by heating to 35-40° C., to which was added activated charcoal (7.5 kg) and the mixture was refluxed for 30 min. The mixture was filtered and filtrate was concentrated to give product having purity between 97-99%.

Example 2

Preparation of Crystalline Form A of Metaxalone

Solid Metaxalone obtained from the Example-1 was dissolved in ethyl acetate (400 lit) at a temperature of between 78-80° C. and further heated to reflux to get a clear solution. The reaction mixture was cooled to a temperature of between 20-35° C. in about 1 hour 15 mins and is then further cooled to temperature between 0-5° C. under stirring. Cubical shaped crystals of Polymorph A were obtained after filtration and drying by conventional methods.

Infrared (IR) Spectroscopy: 1728 cm$^{-1}$.
Differential Scanning Calorimetry (DSC): Melting endotherm at 122.33° C.
X-Ray (powder) Diffraction: Peaks at 4.41, 13.34, and 17.86° 2θ
Shape: Cubical in shape
Purity: 99.5-99.9%

Example 3

Preparation of Crystalline Form B of Metaxalone

Solid Metaxalone obtained from the Example-1 was dissolved in ethyl acetate (400 lit) at a temperature of between 78-80° C. and then further heated to reflux to get a clear solution. The reaction mixture was cooled to a temperature of between 20-35° C. in about 1 hour 45 mins and is then further cooled to temperature between 0-5° C. under stirring. Needle shaped crystals of Polymorph B were obtained after filtration and drying by conventional methods.

Infrared (IR) Spectroscopy: 1753 cm$^{-1}$ and 1772 cm$^{-1}$.
Differential Scanning Calorimetry (DSC): 2 melting endotherms at about 121.5° C. and 122.48° C.
X-Ray (powder) Diffraction: Peaks at 10.26, 14.18, 19.0 and 22.4° 2θ
Shape: Fine needle shaped
Purity: 99.5-99.9%

Example 4

Preparation of Crystalline Form A of Metaxalone

Solid Metaxalone obtained from the Example-1 was dissolved in methyl ethyl ketone (400 lit) at a temperature of between 77-78° C. and further heated to reflux to get a clear solution. The reaction mixture was cooled to a temperature of between 20-35° C. in about 1 hour and is then further cooled to temperature between 0-5° C. under stirring. Cubical shaped crystals of Polymorph A were obtained after filtration and drying by conventional methods.

Infrared (IR) Spectroscopy: 1728 cm$^{-1}$.
Differential Scanning Calorimetry (DSC): Melting endotherm at 122.33° C.
X-Ray (powder) Diffraction: Peaks at 4.41, 13.34, and 17.86° 2θ
Shape: Cubical in shape
Purity: 99.5-99.9%

Example 5

Preparation of Crystalline Form B of Metaxalone

Solid Metaxalone obtained from the Example-1 was dissolved in methyl ethyl ketone (400 lit) at a temperature of between 77-78° C. and then further heated to reflux to get a clear solution. The reaction mixture was cooled to a temperature of between 20-35° C. in about 2 hours and is then further cooled to temperature between 0-5° C. under stirring. Needle shaped crystals of Polymorph B were obtained after filtration and drying by conventional methods.

Infrared (IR) Spectroscopy: 1753 cm$^{-1}$ and 1772 cm$^{-1}$.
Differential Scanning Calorimetry (DSC): 2 melting endotherms at about 121.5° C. and 122.48° C.
X-Ray (powder) Diffraction: Peaks at 10.26, 14.18, 19.0 and 22.4° 2θ
Shape: Fine needle shaped
Purity: 99.5-99.9%

Example 6

Preparation of Crystalline Form A of Metaxalone

Solid Metaxalone obtained from the Example-1 was dissolved in acetonitrile (400 lit) at a temperature of between 78-79° C. and further heated to reflux to get a clear solution. The reaction mixture was cooled to a temperature of between 20-35° C. in about 1 hour 25 mins and is then further cooled to temperature between 0-5° C. under stirring. Cubical shaped crystals of Polymorph A were obtained after filtration and drying by conventional methods.

Infrared (IR) Spectroscopy: 1728 cm$^{-1}$.
Differential Scanning Calorimetry (DSC): Melting endotherm at 122.33° C.

X-Ray (powder) Diffraction: Peaks at 4.41, 13.34, and 17.86° 2θ
Shape: Cubical in shape
Purity: 99.5-99.9%

Example 7

Preparation of Crystalline Form B of Metaxalone

Solid Metaxalone obtained from the Example-1 was dissolved in acetonitrile (400 lit) at a temperature of between 78-79° C. and then further heated to reflux to get a clear solution. The reaction mixture was cooled to a temperature of between 20-35° C. in about 1 hour 45 mins and is then further cooled to temperature between 0-5° C. under stirring. Needle shaped crystals of Polymorph B were obtained after filtration and drying by conventional methods.

Infrared (IR) Spectroscopy: 1753 cm$^{-1}$ and 1772 cm$^{-1}$.

Differential Scanning Calorimetry (DSC): 2 melting endotherms at about 121.5° C. and 122.48° C.

X-Ray (powder) Diffraction: Peaks at 10.26, 14.18, 19.0 and 22.4° 2θ

Shape: Fine needle shaped
Purity: 99.5-99.9%

We claim:

1. A crystalline Metaxalone Form B exhibiting an X-ray (powder) diffraction pattern characterized by 2θ±2 angles and d values as represented in the following table:

| Angle (° 2θ) | d-value (° A) |
|---|---|
| 10.261 | 8.61422 |
| 11.244 | 7.86292 |
| 14.189 | 6.23687 |
| 15.696 | 5.64131 |
| 16.275 | 5.44197 |
| 16.643 | 5.32239 |
| 17.294 | 5.12360 |
| 18.550 | 4.77930 |
| 19.009 | 4.66497 |
| 19.499 | 4.54890 |
| 20.723 | 4.28280 |
| 21.593 | 4.11209 |
| 22.404 | 3.96508 |
| 23.768 | 3.74063 |
| 24.529 | 3.62615 |
| 25.238 | 3.52594 |
| 25.759 | 3.45585 |
| 26.442 | 3.36811 |
| 27.076 | 3.29066 |
| 27.699 | 3.21796 |
| 28.176 | 3.16469 |
| 29.668 | 3.00878 |
| 29.989 | 2.97733 |
| 30.850 | 2.89609 |
| 31.613 | 2.82793 |
| 32.693 | 2.77245 |
| 34.240 | 2.61675 |
| 35.432 | 2.53142 |
| 37.028 | 2.42586 |
| 37.511 | 2.39574. |

2. The crystalline Metaxalone Form B according to claim 1, exhibiting an I.R spectrum with $V^{max}$ at about 1722 cm$^{-1}$ and 1753 cm$^{-1}$ for the carbonyl group.

3. The crystalline Metaxalone Form B according to claim 1, exhibiting an endotherm at about 121.5° C. and 122.48° C. in its Differential Scanning Calorimeter (DSC) thermogram.

4. The crystalline Metaxalone Form B according to claim 1, having a $C_{max}$ value of 40.73±2.8 µg/ml.

5. The crystalline Metaxalone Form B according to claim 1, having a $T_{max}$ value of 2.08±1.4 hr.

6. The crystalline Metaxalone Form B according to claim 1, having a half-life value of 4.49±1.7 hr.

7. The crystalline Metaxalone Form B according to claim 1, having an $AUC_{last}$ value of 333.32±159.9 hrµg/ml; $AUC_{inf}$ value of 389.07±200.6 hrµg/ml; a $MRT_{last}$ value of 5.50±1.8 hr. and a $Cl_{obs}$ value of 472.72±214.7 ml/hr/kg.

* * * * *